United States Patent [19]

Remiszewski

[11] Patent Number: 5,224,929
[45] Date of Patent: Jul. 6, 1993

[54] IRRIGATION/ASPIRATION CANNULA AND VALVE ASSEMBLY

[75] Inventor: Stanley H. Remiszewski, Worcester, Mass.

[73] Assignee: C. R. Bard, Inc., Murray Hill, N.J.

[21] Appl. No.: 632,163

[22] Filed: Dec. 21, 1990

[51] Int. Cl.⁵ .............................................. A61M 1/00
[52] U.S. Cl. ............................... 604/30; 604/35; 604/247; 604/119; 147/596.2; 251/303
[58] Field of Search ............... 604/22, 30, 32, 35, 604/118, 119, 246, 247, 256, 283, 323, 264; 137/596.2, 878; 251/303

[56] References Cited

U.S. PATENT DOCUMENTS

| | | | |
|---|---|---|---|
| 2,415,466 | 2/1947 | Curtis | 251/303 |
| 3,334,655 | 8/1967 | Eppendahl | 137/596.2 |
| 4,027,697 | 6/1977 | Bonney | 137/596.2 |
| 4,134,421 | 1/1979 | Cameron | 251/303 |
| 4,504,266 | 3/1985 | Härle | 604/118 |
| 4,534,758 | 8/1985 | Akers et al. | 604/85 |
| 4,705,073 | 11/1987 | Beck | 137/625.25 |
| 4,781,673 | 11/1988 | Watanabe | 604/9 |
| 4,957,483 | 9/1990 | Gonser et al. | 604/30 |
| 5,011,472 | 4/1991 | Aebischer et al. | 604/50 |
| 5,034,000 | 7/1991 | Freitas et al. | 604/30 |

*Primary Examiner*—John D. Yasko
*Assistant Examiner*—Adam J. Cermak
*Attorney, Agent, or Firm*—Darby & Darby

[57] ABSTRACT

The invention provides an irrigation and aspiration device for use in laparascopic and other types of surgery. When connected to existing irrigation and suction sources, the device provides fingertip control of the fluid connections between the sources and a tube. The device comprises a valve housing with two valve assemblies inside, mounted and configured to take advantage of the static pressure supplied by the sources for increasing seal integrity of the valves. The internal chambers of the valve housing are also configured such that when one valve is open, the pressure differential across the other valve is increased, further increasing its seal integrity.

13 Claims, 2 Drawing Sheets

IRRIGATION/ASPIRATION CANNULA AND VALVE ASSEMBLY

BACKGROUND OF THE INVENTION

This invention relates to irrigation/aspiration equipment.

This invention is more particulary concerned with irrigation/aspiration equipment used in a hand-held manner in a surgical setting for delivering fluid to an internal body site and removing the fluid and other debris from the same site.

Suction-irrigation cannulas are common in various configurations. They are used during surgical procedures on relatively inaccessible areas of the body, such as the interior of the eye, or in connection with laparascopic surgery and diagnostic procedures. Some of these devices have complex valve arrangements for regulating the flow from existing sources, i.e., irrigation pumps and suction units.

Current irrigation/aspiration cannulas available are known to have valving problems. These cannulas have a tendency to leak across their valves from the constant pressure differential supplied by the irrigation/suction sources. The valves also occasionally stick in one position. These deficiencies are due to the valve designs, which rely on a precise mechanical interference, e.g., sliding trumpet valves or rotary ball-style valves, that are adversely affected by the static pressure of the sources. These valve designs also create complex fluid flow paths, compromising the transfer of fluids to and from the surgical area.

A typical example is shown in U.S. Pat. No. 4,526,573, which discloses a device for controlling the delivery of irrigation or suction to a surgical site. This device includes a trumpet valve to selectively connect either the suction or irrigation line to an outlet port. Closing either line is accomplished by operating the trumpet valve so as to position one of two resilient elastomeric flanges at either end of a waisted valve member to a position between the supply line port desired to be closed and the outlet port. In this configuration, static pressure in both the suction and irrigation supply lines tends to promote leakage across the elastomeric flange, and one could expect the problem to get worse over time as the flanges wear out.

U.S. Pat. No. 4,668,215 discloses another valving system for an automatic irrigation and evacuation device for use in laparascopic procedures and general surgery. In this device, which makes use of ball-type valves, it is again seen that O-rings are used to provide sealing between the irrigation and suction supplies. A relief port is provided to minimize (but not eliminate) the pressure differential across the O-rings during operation, but again, it can be expected that operation of the valve mechanism degrades over time as the 0-rings wear out.

SUMMARY OF THE INVENTION

In view of the difficulties faced with the presently available valve systems, it is an object of the invention to provide an improved irrigation/aspiration cannula, wherein valve wear caused by static pressure differentials is eliminated, and the differentials are used to advantage in the functioning of the valves. In fact, as the pressure differential increases, within reasonable limits, the seal integrity of the valves increases.

It is a further object of the invention to make the cannula more resistant, by design, to fluctuations in manufacturing tolerances, thus improving its economy.

It is a further object of the invention to make the cannula hand-held and easily finger-actuated to give superior tactile sensation and control during surgery.

It is a further object of the invention to make the cannula relatively inexpensive and compatible with standard surgical equipment.

It is a further object of the invention that the fluid flow path through the device has very shallow turns, improving fluid flow quality.

In the invention, a valve body is constructed to have internal chambers and valve assemblies that allow selective fluid communication between a tube and two fluid sources, i.e., an irrigation pump and a vacuum pump. These valve assemblies are sealed by the hydrostatic pressure differentials, created by the fluid sources, across the valve assemblies.

The foregoing and other objects and advantages of this invention will become apparent to those skilled in the art upon reading the detailed description of a preferred embodiment in conjunction with a review of the appended drawings.

DETAILED DESCRIPTION

Figure 1:
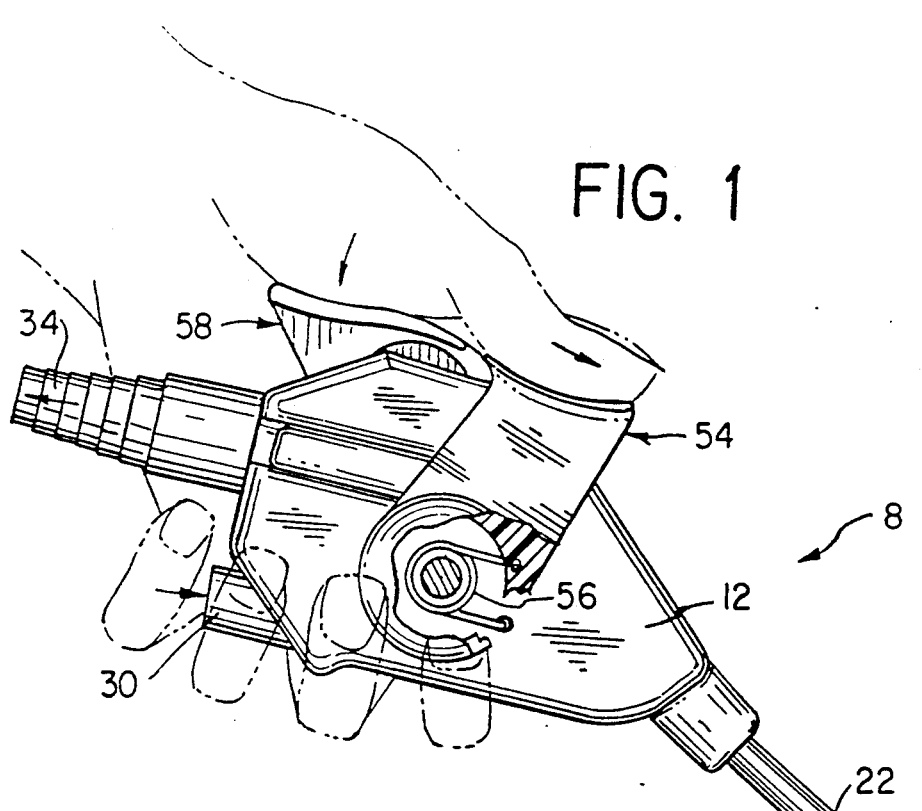
FIG. 1 is an elevational view of the improved cannula, showing an operator's hand in position.

In the preferred embodiment, an irrigation/aspiration cannula 8 includes a valve body 10, constructed with a valve body cover 12. Together, the valve body 10 and the valve body cover 12 form one common inner chamber 14, an inlet chamber 16 and an outlet chamber 18. A tube 22 is connected to the inner chamber 14, through an aperture 20 in the valve body 10. The tube 22 has at least one inlet/outlet hole 24 at its distal end and an axial bore 26. Other configurations of the tube 22 are possible, including interchangeable tips at its distal end.

An irrigation adapter 30 is integrally molded to the valve body 10 and is connected to the inlet chamber 16 through an inlet aperture 28. The irrigation adapter 30 is adapted for connection to common surgical irrigation sources, such as those with a LUER connector-type lock. Integrally molded to the valve body 10 is a suction adapter 34, which is connected to the outlet chamber 18 through an outlet aperture 32 and is adapted for connection to common surgical suction sources. In a nonpreferred embodiment, the irrigation adapter 30 and suction adapter 34 may be separate units that are attached to the valve body 10.

Connecting inner chamber 14 and inlet chamber 16 is an inlet valve port 36, which can be covered and sealed by a seal button 38, made of a resilient substance, preferably a polymeric substance such as C-FLEX® R70-050 available from Concept Polymer Technologies, Clearwater, Fla. Connecting the inner chamber 14 and the outlet chamber 18 is an outlet valve port 40, which can be covered and sealed by a seal button 42.

The two seal buttons 38 and 42 each have a narrowed midsection 44, allowing them to be connected to a pair of valve flappers 48 and 46, respectively. The valve flapper 46 is rotatably mounted on a lever shaft 50 so that the seal button 42 will completely cover and seal the outlet port 40, when the flapper 46 is in its closed position. The valve flapper 48 is mounted rotatably on a lever shaft 52 so that the seal button 38 will completely cover and seal the inlet port 36 when the flapper 48 is in its closed position.

An irrigation lever 54 is rotatably mounted on the outside of the valve body cover 12 by the lever shaft 52 and connected by the lever shaft 52 to the valve flapper 48. A return spring 56 is mounted on the lever shaft 52 and anchored to the valve body cover 12 and the irrigation lever 54. An aspiration lever 58 is rotatably mounted on the outside of the valve body 10 by the lever shaft 50 and connected by the lever shaft 50 to the valve flapper 46. A return spring 60 is mounted on the lever shaft 50 and anchored to the valve body 10 and the aspiration lever 58.

A O-ring 62 is mounted in the sidewall of the valve body cover 12 and around the lever shaft 50 to maintain a seal while allowing the lever shaft 50 to rotate. An O-ring 64 is mounted in the sidewall of the valve body 10 and around the lever shaft 52.

At the beginning of operation of the device, both seal buttons 38 and 42 will cover and seal their respective ports 36 and 40. Assuming both the external suction and irrigation pumps are operational, pressure differentials will exist across the two ports 36 and 40. The pressure (atmospheric) in the inner chamber 14 will be higher than in the outlet chamber 18. This higher pressure exerts a force on the seal button 42 in the direction of the outlet port 40, tightening the seal therein. Similarly, the pressure in the inlet chamber 16 will be higher than in inner chamber 14. This higher pressure will exert a force on the seal button 38 in the direction of inlet port 36, tightening the seal therein.

To transfer irrigation fluid to the tube 22 and the surgical site, the operator exerts finger pressure on the irrigation lever 54 and rotates it clockwise. This rotates the lever shaft 52, which rotates the valve flapper 48 and lifts the seal button 38 off the inlet port 36, allowing fluid to pass from the inlet chamber 16 into the inner chamber 14, then into the tube 22 and the surgical site. One result of this fluid transfer is to increase the static pressure in the inner chamber 14, increasing the force exerted on the seal button 42, further increasing the integrity of the seal over the outlet port 40. When a proper amount of irrigation fluid has been expelled through the tube 22, the operator releases finger pressure on the irrigation lever 54. The combined force of the return spring 56 and the continued pressure differential across the inlet port 36 will cause the seal button 38 to cover and seal the inlet port 36, automatically cutting off the fluid flow from the external irrigation pump to the tube 22.

To remove fluid by suction from the surgical site through the tube 22, the operator exerts palm pressure on the aspiration lever 58 and rotates it counterclockwise. This rotates the lever shaft 50, which rotates the valve flapper 46 and lifts the seal button 42 off the outlet port 40, allowing fluid to be drawn up from the surgical site into the tube 22, through the inner chamber 14, through the outlet chamber 18 and out the outlet aperture 32. One result of this fluid transfer is to decrease the static pressure in the inner chamber 14, increasing the force exerted on the seal button 38 and tightening the seal over the inlet port 36. When a proper amount of fluid has been drawn up through the tube 22, the operator releases pressure on the aspiration lever 58. The combined force of the return spring 60 and the continued pressure differential across the outlet port 40 will cause the seal button 42 to cover and seal the outlet port 40, automatically cutting off the fluid flow from the tube 22 to the external vacuum pump (not shown).

Figure 2:
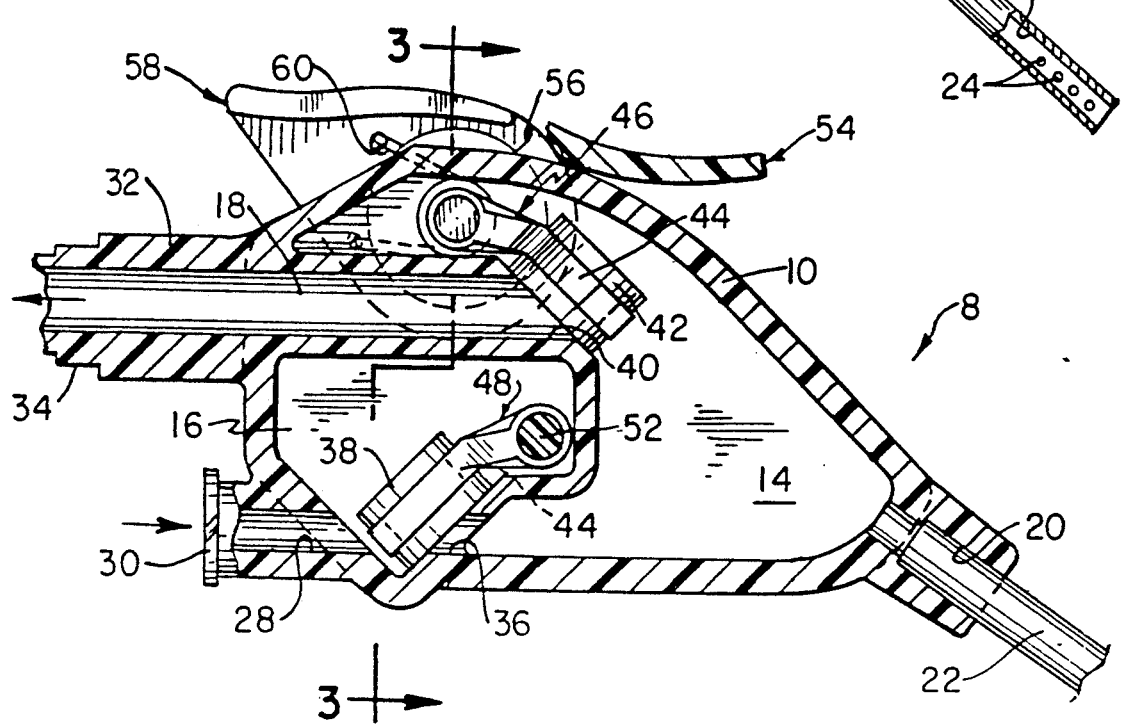
FIG. 2 is a sectional view of the improved cannula, showing the internal chambers and valve assemblies.
Figure 3:
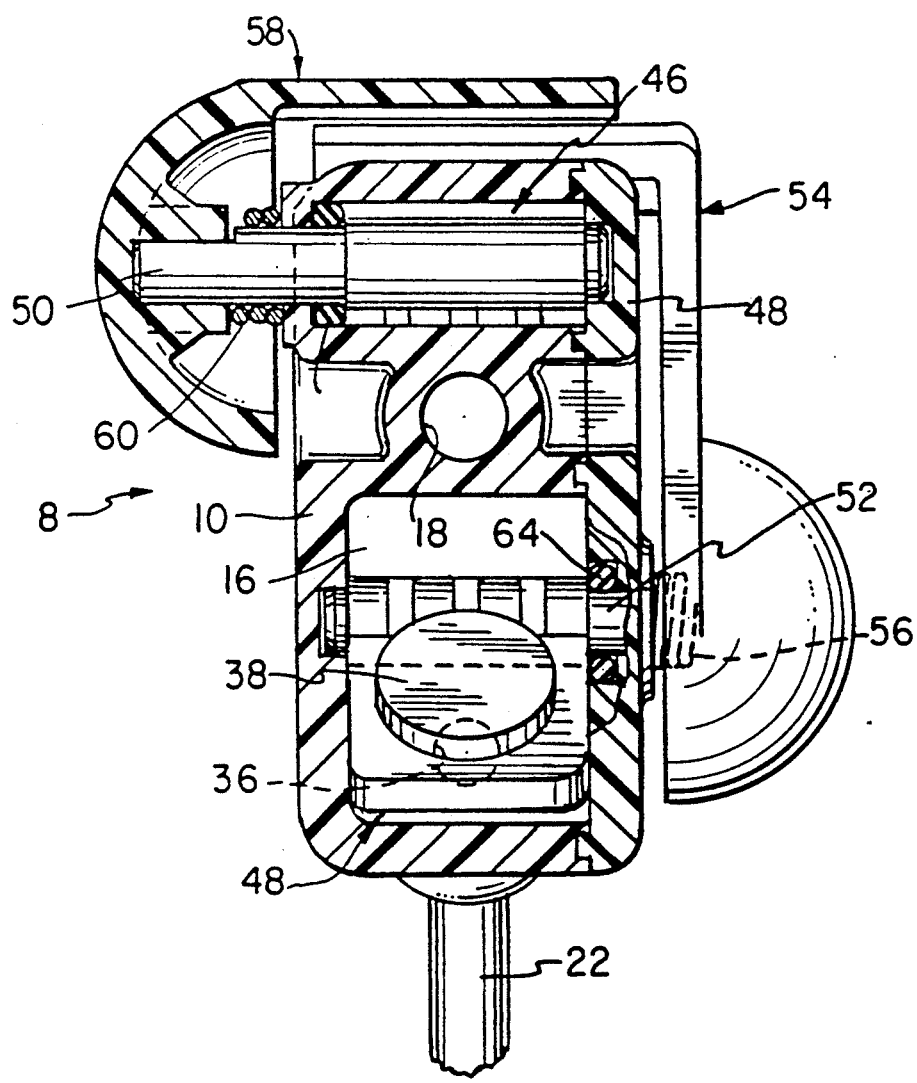
FIG. 3 is a sectional view of the improved cannula, showing a valve assembly in its closed position.

In the preferred embodiment, the valve body 10 and valve body cover 12 are sealed with epoxy, eliminating any leakage problems. Within the valve body 10, the inner chamber 14 and the inlet and outlet chambers 16 and 18 are designed for nearly straight-path fluid flow from the tube 22 to the suction and irrigation sources (not shown). As disclosed in the specific embodiment illustrated in FIG. 2, fluid flowing through the valve body 10 of the preferred embodiment will only be required to make turns in its path of less than 90°, i.e., obtuse angles between adjacent flow path segments. This decreases fluid resistance and thus raises the quality and rate of the fluid flow. The tube 22 is preferably stainless steel and has an axial bore 26 and multiple outlet/inlet holes 24 at its distal end. However, tubes of various designs or suited for various purposes utilizing irrigation and suction are also appropriate.

The valve flappers 46 and 48 use a "floating" seal, wherein the seal buttons 38 and 42 have a radius significantly larger than the valve ports 36 and 40, allowing for some shifting during operation and greater tolerances during manufacture, without compromising seal integrity.

While the embodiment of the invention shown and described is fully capable of achieving the results desired, it is to be understood that this embodiment has been shown and described for purposes of illustration only and not for purposes of limitation.

What is claimed is:

1. An irrigation/aspiration cannula, which comprises:
   a tube;
   a valve housing connected to the tube, said housing having a fluid inlet aperture and a fluid outlet aperture, said housing allowing fluid communication between the tube, the fluid inlet aperture and the fluid outlet aperture;
   means for connecting said fluid inlet aperture to a pressurized fluid source and for connecting said fluid outlet aperture to a vacuum source, said means providing a releasable and substantially fluid-tight connection; and
   a plurality of valve assemblies for selectively connecting only one of the apertures to the tube at any given moment, mounted and located within the housing such that hydrostatic pressure differentials across the valve assemblies seal the valve assemblies when at least one of the apertures is connected to its respective source.

2. An irrigation/aspiration cannula as in claim 1, wherein each of the valve assemblies has an open position and a closed position, such that when one of the valve assemblies is in the open position, the pressure differential across the other valve assembly increases, increasing the sealing performance of the other valve assembly.

3. An irrigation/aspiration cannula which comprises:
   a tube;
   a valve housing connected to the tube, said housing having a fluid inlet aperture adapted to be connected to a pressurized fluid source and a fluid outlet aperture adapted to be connected to a vacuum source, said housing allowing fluid communication between the tube, the fluid inlet aperture and the fluid outlet aperture;

a plurality of valve assemblies for selectively connecting only one of the apertures to the tube at any given moment, mounted and located within the housing such that hydrostatic pressure differentials across the valve assemblies seal the valve assemblies when at least one of the apertures is connected to its respective source;

wherein the valve housing has a common interior chamber, connected to the tube, the valve housing also having ports through which the chamber is connected to the inlet aperture and the outlet aperture.

4. An irrigation/aspiration cannula as in claim 3, wherein the interior chamber is constructed so that the flow path through the cannula has only obtuse angles.

5. An irrigation/aspiration cannula as in claim 1, wherein said means for connecting is integral with said valve housing.

6. An irrigation/aspiration cannula as in claim 1, wherein the tube has an axial bore and at least one outlet/inlet hole at its distal end for irrigation/aspiration of an area of tissue under surgery.

7. An irrigation/aspiration cannula as in claim 1, wherein the valve housing comprises a valve body and a valve body cover.

8. An irrigation/aspiration cannula as in claim 1, wherein there are two valve assemblies.

9. An irrigation/aspiration cannula as in claim 3, wherein the valve assemblies incorporate a floating seal-type valve.

10. An irrigation/aspiration cannula as in claim 9, wherein each valve assembly comprises a seal button retained by a valve flapper, the seal button positioned to cover and seal one of the ports leading from one of the apertures into the common interior chamber.

11. An irrigation/aspiration cannula, which comprises:

a tube;

a valve housing connected to the tube, said housing having a fluid inlet aperture adapted to be connected to a pressurized fluid source and a fluid outlet aperture adapted to be connected to a vacuum source, said housing allowing fluid communication between the tube, the fluid inlet aperture and the fluid outlet aperture;

a plurality of valve assemblies for selectively connecting only one of the apertures to the tube at any given moment, mounted and located within the housing such that hydrostatic pressure differentials across the valve assemblies seal the valve assemblies when at least one of the apertures is connected to its respective source wherein each valve assembly further comprises a lever on the outside of the housing, each valve assembly being actuated by the lever.

12. An irrigation/aspiration cannula as in claim 11, further comprising spring means wherein each of the levers are automatically returned to a starting position by the spring means, each of the levers also returning the respective valve assembly to the closed position.

13. An irrigation/aspiration cannula, as in claim 12, wherein the levers are connected to the valve flappers by lever shafts that penetrate the valve housing wall.

* * * * *